(12) United States Patent
Merriman (10) Patent No.: US 9,162,181 B1
(45) Date of Patent: Oct. 20, 2015

(54) PROBE ASSEMBLY

(71) Applicant: Dale C. Merriman, Houston, TX (US)

(72) Inventor: Dale C. Merriman, Houston, TX (US)

( * ) Notice: Subject to any disclaimer, the term of this patent is extended or adjusted under 35 U.S.C. 154(b) by 0 days.

(21) Appl. No.: 14/602,252

(22) Filed: Jan. 21, 2015

Related U.S. Application Data (60) Provisional application No. 62/037,011, filed on Aug. 13, 2014.

(51) Int. Cl.
  *G01N 15/06* (2006.01)
  *G01N 33/00* (2006.01)
  *B01D 53/86* (2006.01)

(52) U.S. Cl.
  CPC .......... *B01D 53/864* (2013.01); *G01N 33/0009* (2013.01); *B01D 2255/1021* (2013.01)

(58) Field of Classification Search
  CPC ........ G01N 15/06; G01N 33/00; G01N 33/48
  USPC .......................................... 422/83, 89, 94, 98
  See application file for complete search history.

(56) References Cited

U.S. PATENT DOCUMENTS

| | | | |
|---|---|---|---|
| 2007/0137318 A1* | 6/2007 | Desrochers et al. | 73/863.81 |
| 2009/0211368 A1* | 8/2009 | Garnett et al. | 73/861.22 |
| 2011/0122918 A1* | 5/2011 | Murray | 374/208 |
| 2014/0269820 A1* | 9/2014 | Perrault et al. | 374/54 |

* cited by examiner

*Primary Examiner* — Brian J Sines
(74) *Attorney, Agent, or Firm* — Buskop Law Group, PC; Wendy Buskop (57) ABSTRACT

A probe assembly for processing an outlet gas from a gas analyzer. The probe assembly has a thermowell and a heating element mounted in the thermowell connecting to a power connection, wherein the heating element heats the thermowell. The probe assembly has a one piece non-sintered metal probe with an end cap smaller than a tubular body inner diameter, a plurality of upper longitudinal outer grooves and a plurality of longitudinal slots, or a plurality of perforations. The probe assembly has a street tee with an inlet port to receive outlet gas from the gas analyzer and a sintered metal outer housing, through a catalyst cartridge for reaction. This reaction produces water vapor and carbon dioxide while simultaneously allowing ambient air to enter the catalyst cartridge while exhausting water vapor and carbon dioxide at a continuous flow rate.

17 Claims, 8 Drawing Sheets

PROBE ASSEMBLY

CROSS REFERENCE TO RELATED APPLICATIONS

The present application claims priority to and the benefit of U.S. Provisional Patent Application Ser. No. 62/037,011 filed on Aug. 13, 2014, entitled "PROBE ASSEMBLY". This reference is hereby incorporated in its entirety.

FIELD

The present embodiments generally relate to a probe assembly for treating outlet gas from gas analyzers.

BACKGROUND

A need exists to treat gases with volatile carrier gases from gas analyzers quickly, safety and continuously.

The present embodiments meet these needs.

BRIEF DESCRIPTION OF THE DRAWINGS

The detailed description will be better understood in conjunction with the accompanying drawings as follows.

The present embodiments are detailed below with reference to the listed Figures.

DETAILED DESCRIPTION OF THE EMBODIMENTS

Before explaining the present apparatus in detail, it is to be understood that the apparatus is not limited to the particular embodiments and that it can be practiced or carried out in various ways.

A benefit of the invention is a probe assembly that meets the changes demanded by analyzer manufacturers for a probe that can withstand problems with hydrogen carrier gasses. Nitrogen carrier probes have not been able to withstand the corrosiveness of the hydrogen carrier gas, and the present probe design was needed. The sintered metal design outer housing of the probe assists in removing heat from the probe while simultaneously acting as a flame arrestor for the probe assembly.

The new probe assembly reduces down time for gas analysis and replacement costs which are significant over currently available commercial probes.

The current probe assembly provides a significant environmental advantage by operating correctly much longer than nitrogen carrier probes and by not allowing harmful fugitive emissions into the atmosphere.

The probe assembly does not compromise safety in the field. The probe assembly reduces the possibility of explosions and death in the field which can occur when a nitrogen carrier probe assembly is used with hydrogen carrier gasses. Reducing death in the field and reducing the chance of fires in the field is a significant benefit of the present probe assembly device.

The probe assembly contributes to the safety in petrochemical complexes by having a life expectancy at least 300 times longer than the average probe which uses nitrogen or other non-volatile carriers.

The embodiments relate to a probe assembly for processing a gas having a volatile carrier gas from a gas analyzer.

The probe assembly can have a thermowell and a heating element mounted in the thermowell connected to a power connection. The heating element can heat the thermowell. A one piece non-sintered metal probe can have a tubular body that surrounds the thermowell. The one piece non-sintered metal probe can be integral with a mounting nut on one end of the tubular body and an end cap formed on the other end of the tubular body.

The end cap can have an end cap inner bore. The end cap inner bore has an end cap inner bore diameter which can be at least 10 percent smaller than a tubular body inner diameter. In embodiments, the end cap inner bore diameter can be 10 percent to 80 percent smaller than a tubular body inner diameter. In some cases, the end cap inner bore diameter can from about 20 millimeters to about 75 millimeters in diameter.

A plurality of upper longitudinal outer grooves and longitudinal slots can penetrate the tubular body.

A catalyst cartridge can cover the tubular body. A street tee with an inlet port can flow outlet gas from the gas analyzer into a sintered metal outer housing surrounding the non-sintered metal probe, through the catalyst cartridge for reaction, producing water vapor and carbon dioxide while simultaneously allowing ambient air to enter the catalyst cartridge while exhausting carbon dioxide and water vapor at a continuous flow rate from about 200 milliliters to about 1000 milliliters per minute.

The catalyst cartridge can react the gas from a flow rate as low as 0.1 milliliters to 1 liter per minute.

The probe assembly produces (i) zero backpressure of outlet gas to the gas analyzer or (ii) outlet gas at a constant value while (iii) continuously flowing outlet gas into the probe assembly for continuous conversion of the outlet gas to water vapor and carbon dioxide at a rate up to 1 liter per minute in most embodiments.

The sintered metal outer housing is critical in that it provides heat dissipation for the probe. The sintered metal outer housing is used to act as a flame arrestor and prevent fire caused by the probe's use. The sintered metal outer housing provides protection of both heat dissipation and flame arresting simultaneously which is a remarkable safety benefit.

The probe assembly functions to prevent toxic emission from gas analyzers that measure hydrocarbons by catalytically converting the dangerous and polluting gases into harmless water vapor and carbon dioxide.

The invention can protect the air around chemical plants, refineries, and other manufacturing trains that use hydrocarbons as a feed stock or end product.

The invention protects workers at a site by reducing hydrocarbon emissions, which in some quantities can cause cancer and death.

Figure 1:
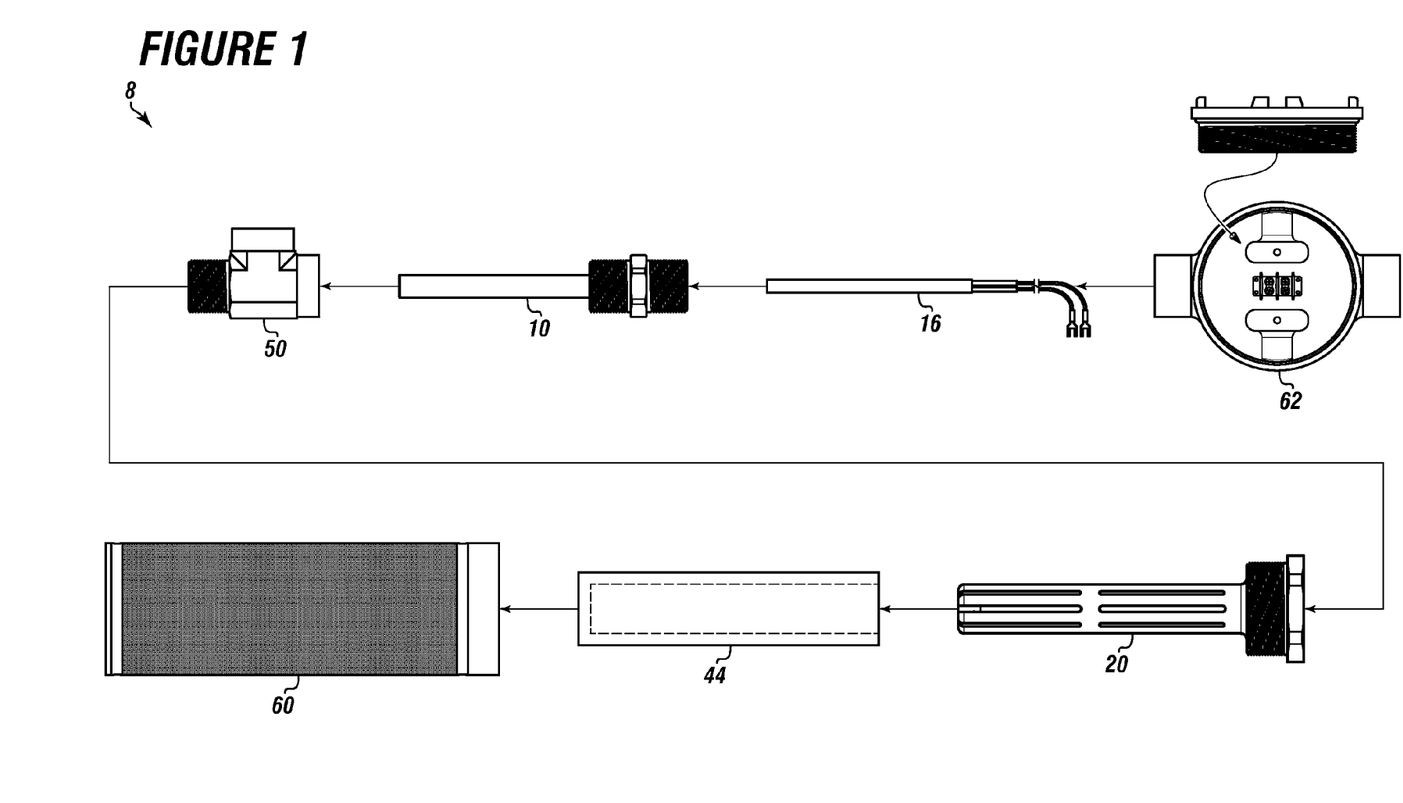
FIG. 1 depicts an assembly view of a probe assembly.

Turning now to the Figures, FIG. 1 depicts an assembly view of the probe assembly. The probe assembly can be used for engaging a gas outlet from a gas analyzer, wherein gas from the gas analyzer uses a volatile carrier gas.

The probe assembly 8 can include a junction box 62, a heating element 16, a thermowell 10, a street tee 50, a one piece non-sintered metal probe 20, a catalyst cartridge 44 and a sintered metal outer housing 60.

The thermowell 10 can have a thermowell bore. The heating element 16 can be adapted to mount in the thermowell bore. The heating element 16 can connect to a power connection in the junction box 62. When energized, the heating element 16 can heat the thermowell 10.

The street tee 50 can accept the thermowell 10 through a first tee end. The street tee can have an inlet port adapted to receive outlet gas from a gas analyzer. The street tee 50 can thread into an inner bore of the one piece non-sintered metal probe 20 having a tubular body.

The catalyst cartridge 44 can receive the one piece non-sintered metal probe 20, wherein the tubular body can snugly fit within a central cavity of the catalyst cartridge. The tubular body can have an interference fit within the central cavity. An interference fit, also known as a press fit or friction fit, is a fastening between two parts which can be achieved by friction after the parts are pushed together, rather than by any other means of fastening.

The sintered metal outer housing 60 can threadably engage outer threads of the one piece non-sintered metal probe while simultaneously enclosing the catalyst cartridge, enabling outlet gas from a gas analyzer containing hydrocarbon products with a volatile carrier gas to be continuously flowed between the thermowell and the tubular body of the one piece non-sintered metal probe into the catalyst cartridge for reaction. This reaction produces water vapor and carbon dioxide while the sintered metal outer housing simultaneously allows two-way gas flow of ambient air to the catalyst cartridge while exhausting carbon dioxide and water vapor to atmosphere.

The probe assembly 8 produces no additional backpressure of outlet gas to the gas analyzer or to a constant value creating a continuous flow rate of outlet gas for conversion to carbon dioxide and water vapor at a volume from about 200 milliliters to about 1 liter per minute.

Figure 2A:
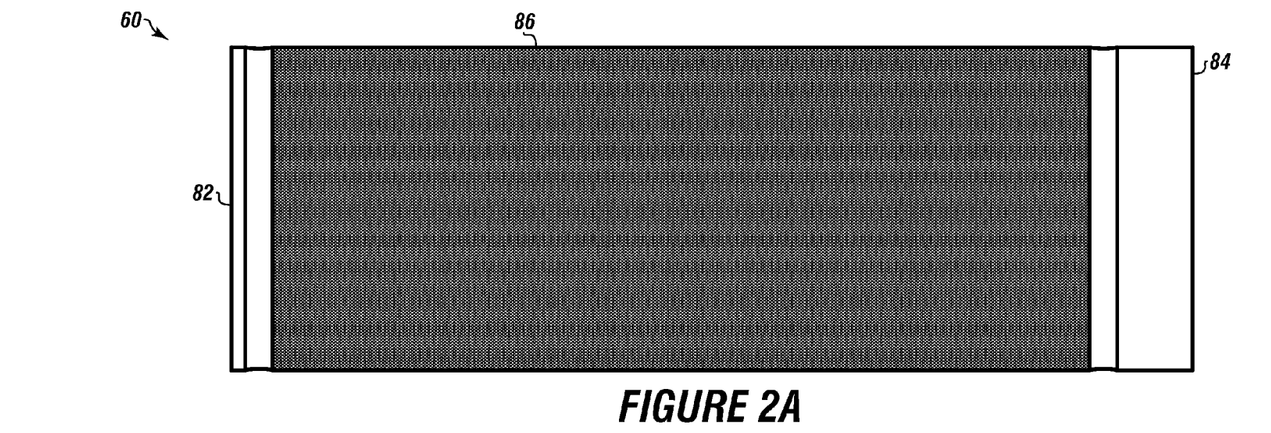
FIG. 2A depicts a perspective view of a sintered metal outer housing.

FIG. 2A depicts a perspective view of the sintered metal outer housing.

The sintered metal outer housing 60 can have a non-sintered solid end cap 82, a non-sintered solid threaded end cap 84, and a sintered metal central portion 86. In embodiments, the sintered metal central portion 86 can be between the non-sintered solid end cap 82 and the non-sintered solid threaded end cap 84.

In embodiments, the sintered metal central portion can have 100 percent sintered metal walls ranging in thickness from about ⅛ of an inch to about ½ of an inch.

Figure 2B:
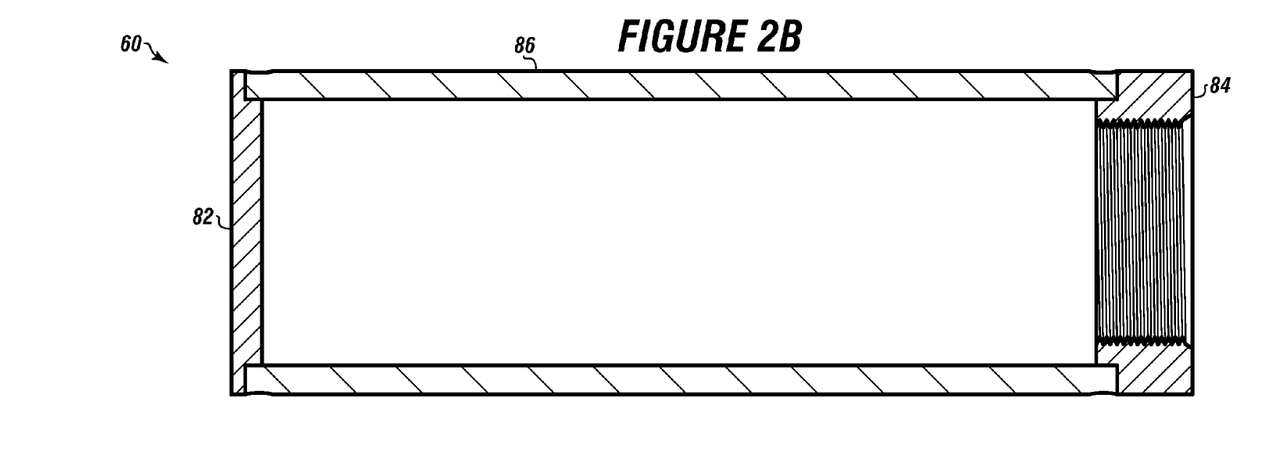
FIG. 2B depicts a cross sectional view of the sintered metal outer housing.

FIG. 2B depicts a cross sectional view of the sintered metal outer housing.

The sintered metal outer housing 60 can have inner threads forming an inner chamber, the non-sintered solid end cap 82, and the non-sintered solid threaded end cap 84. The sintered metal central portion 86 can be between the non-sintered solid end cap and the non-sintered solid threaded end cap.

Figure 3:
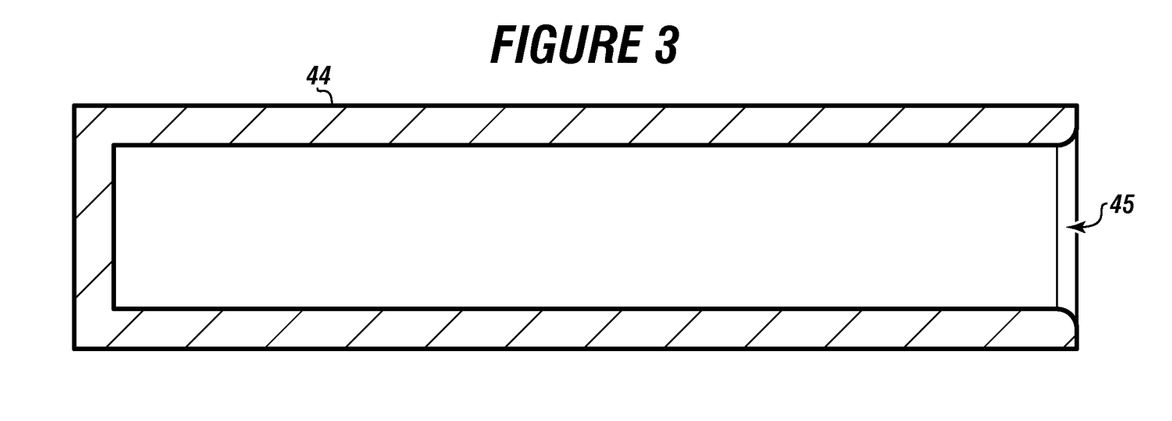
FIG. 3 depicts a cross sectional view of a catalyst cartridge.

FIG. 3 depicts a cross sectional view of the catalyst cartridge.

The catalyst cartridge 44 can have a central cavity 45. The tubular body of the one piece non-sintered metal probe can fit snugly within the central cavity of the catalyst cartridge.

In embodiments, the catalyst cartridge can be a ceramic wool supported platinum catalyst having a cylindrical shape with an enclosed end cap.

Figure 4A:
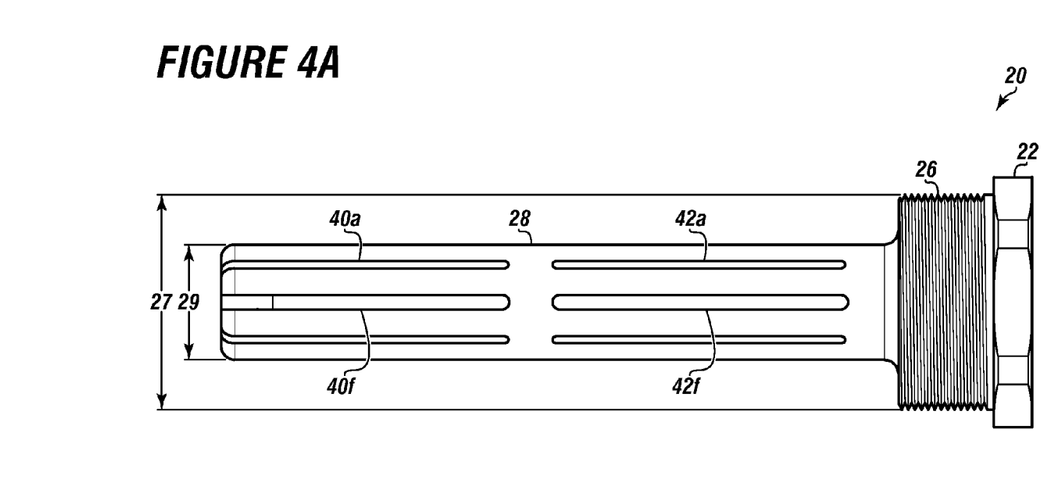
FIG. 4A depicts a side perspective view of a one piece non-sintered metal probe.
Figure 4B:
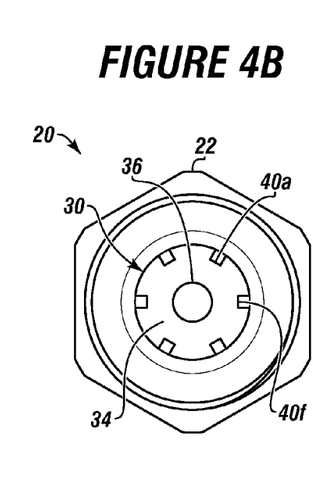
FIG. 4B depicts a top view of the one piece non-sintered metal probe.
Figure 4C:
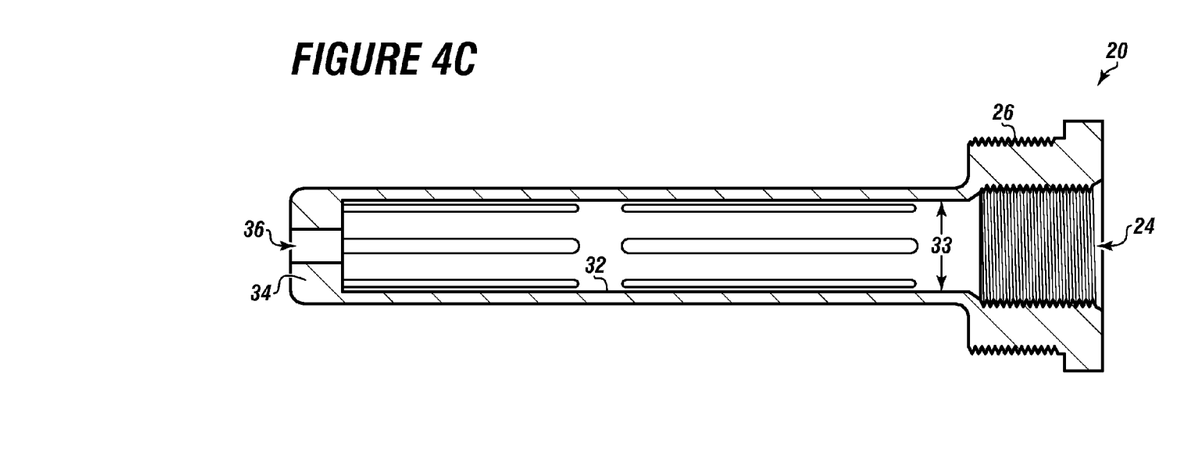
FIG. 4C depicts a cross sectional view of the one piece non-sintered metal probe.

FIG. 4A depicts a side perspective view of the one piece non-sintered metal probe. FIG. 4B depicts a top view of the one piece non-sintered metal probe. FIG. 4C depicts a cross sectional view of the one piece non-sintered metal probe.

Referring to FIGS. 4A-4C, the one piece non-sintered metal probe 20 can have an inner threaded bore 24 and outer threads 26 proximate a mounting nut 22. The mounting nut 22 can have the largest diameter of the one piece non-sintered metal probe 20.

The one piece non-sintered metal probe 20 can have a tubular body 28 with a tubular body outer diameter 29. The tubular body outer diameter can be from about 10 percent to about 40 percent less than an outer thread outer diameter 27. In some embodiments, it may be only from 1 percent to 9 percent less in diameter. In many embodiments, the tubular body outer diameter can be from 15 percent to 25 percent less than the outer thread outer diameter 27.

The tubular body 28 can be adapted to be integral with the mounting nut 22. The tubular body can have an outer surface 30, a tubular body inner bore 32, and an end cap 34 with an end cap inner bore 36.

The end cap inner bore 36 can fluidly connect to the tubular body inner bore 32. The end cap inner bore 36 can be at least 10 percent smaller than a tubular body inner diameter 33.

A plurality of upper longitudinal outer grooves 40a-40f can be formed equidistantly around the end cap 34 with at least 50 percent and up to 100 percent of each of a plurality of upper longitudinal outer groove penetrating into the tubular body inner bore 32 without penetrating into the end cap inner bore 36. In embodiments, the plurality of upper longitudinal outer groove may penetrate into the tubular body inner bore less than 50 percent. The plurality of upper longitudinal outer grooves in certain uses may assist in flowing fluid and/or particulate away from the probe assembly to prevent clogging and malfunction.

In other embodiments, the plurality of upper longitudinal outer grooves may not be positioned equidistantly around the tubular body. In other embodiments, perforations and grooves can be used.

For the purposes of this application, the terms "slots" and "grooves" can be used to refer to similar perforations with only 1 millimeter or 2 millimeters of opening extending parallel to the longitudinal axis of the tubular body inner bore.

A plurality of longitudinal slots 42a-42f can be formed equidistantly around the tubular body, each of the plurality of longitudinal slots extending from the outer surface 30 to the tubular body inner bore 32.

In embodiments, the one piece non-sintered metal probe can have from 4 to 8 upper longitudinal outer grooves. In embodiments, the one piece non-sintered metal probe can have from 4 to 8 longitudinal slots. In embodiments, the plurality of upper longitudinal outer grooves can be aligned with the plurality of longitudinal slots.

In embodiments, the one piece non-sintered metal probe can comprise a tubular non-ferrous corrosion resistant material, such as a ceramic material.

Figure 4D:
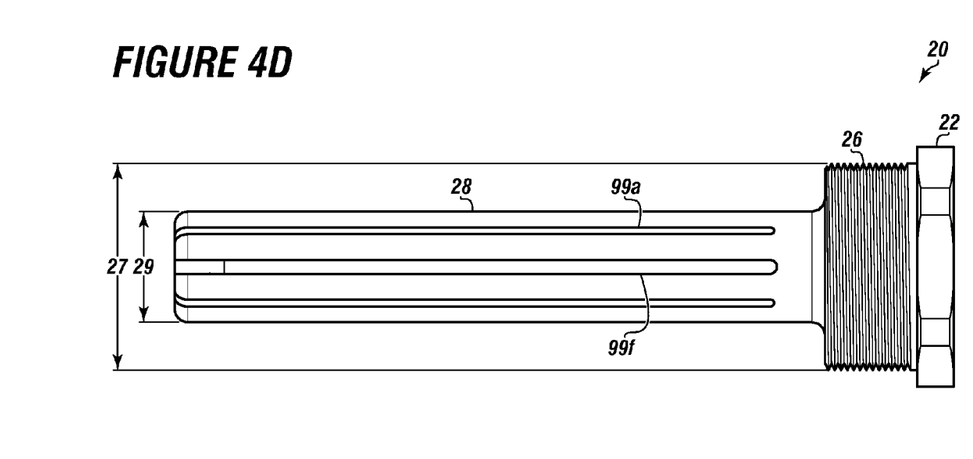
FIG. 4D depicts a side perspective view of a one piece non-sintered metal probe with individual grooves instead sets of grooves formed in the outer surface.

FIG. 4D shows that in an embodiment, the probe assembly's plurality of upper longitudinal outer grooves and plurality of longitudinal slots can be replaced by a plurality of individual slots 99a-99f extending from the end cap to the tubular body inner bore.

Figure 4E:
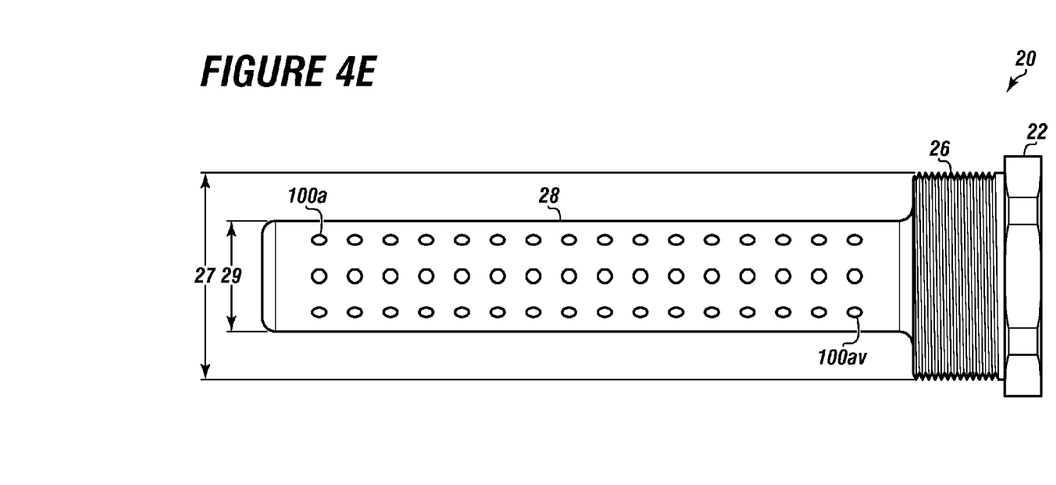
FIG. 4E depicts a side perspective view of a one piece non-sintered metal probe with a plurality of perforations formed in the outer surface.

FIG. 4E shows that in an embodiment, the probe assembly's plurality of upper longitudinal outer grooves and plurality of longitudinal slots can be replaced with a plurality of perforations 100a-100av.

In embodiments, the plurality of perforations can be formed equidistantly around the end cap penetrating to the tubular body inner bore penetrating to the end cap inner bore.

The plurality of perforations can have a shape selected from the group: elliptical, round, square, and/or another polygonal shape.

The plurality of perforations can penetrate at least 50 percent of the tubular body outer diameter.

The plurality of perforations can have a width or diameter from about 0.1 of a millimeter to about 1 centimeter.

Figure 5A:
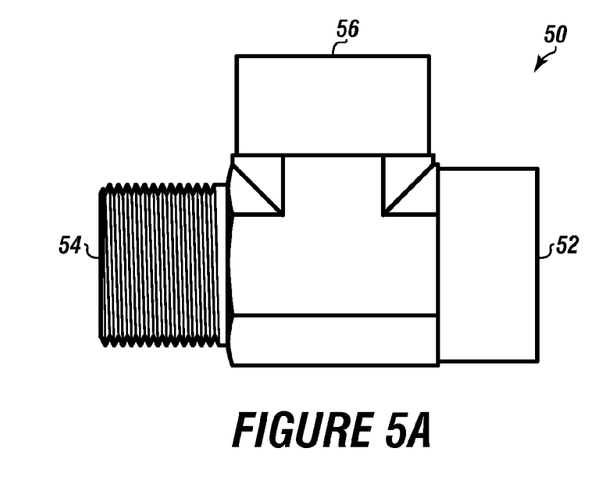
FIG. 5A depicts a perspective view of a street tee.
Figure 5B:
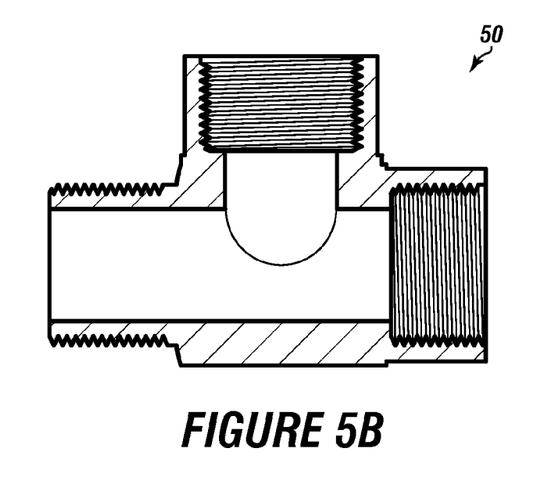
FIG. 5B depicts a cross sectional view of the street tee.

FIG. 5A depicts a perspective view of the street tee. FIG. 5B depicts a cross sectional view of the street tee.

Referring to FIGS. 5A and 5B, the street tee 50 can have a first tee end 52 and a second tee end 54 aligned longitudinally with the first tee end. An inlet port 56 can be formed at a 90 degree angle to the first and second tee ends.

The first tee end 52 can be adapted to thread to the thermowell. The second tee end 54 can threadably engage the inner threaded bore of the mounting nut. The inlet port 56 can be adapted to receive outlet gas from a gas analyzer.

Figure 6:
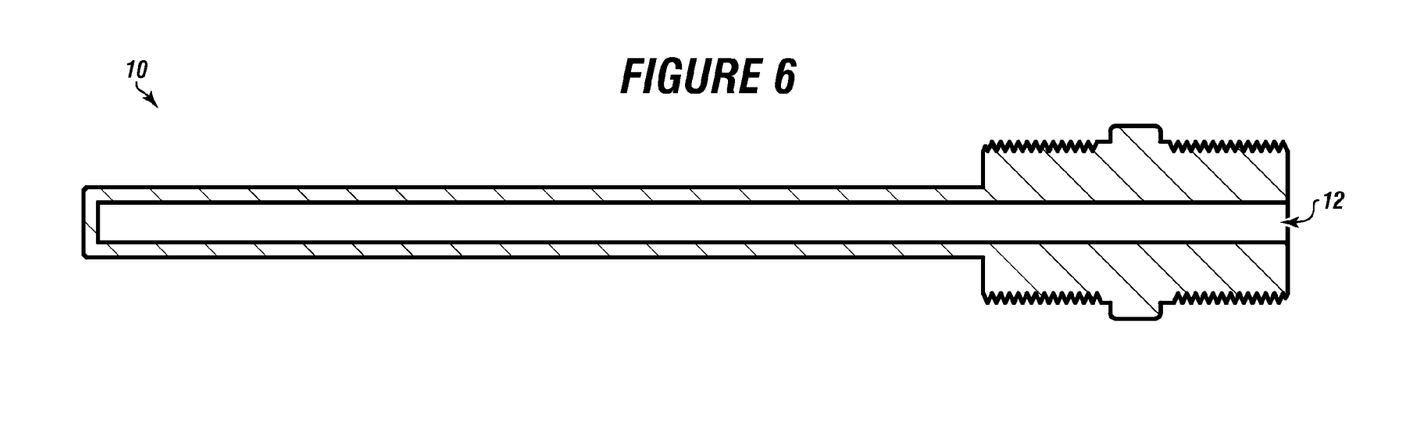
FIG. 6 depicts a cross sectional view of a thermowell.

FIG. 6 depicts a cross sectional view of the thermowell.

The thermowell 10 can have a thermowell bore 12. The heating element can fit snugly within the thermowell bore.

In embodiments, the thermowell and the one piece non-sintered metal probe can be stainless steel, titanium, other alloys of corrosion resistant material, ceramic, ceramic and glass, similar materials, and combinations thereof.

In embodiments, the thermowell bore can have an inner diameter from about 1/16 of an inch to about 1/4 of an inch. In further embodiments, the thermowell can have a length from about 7 inches to about 12 inches.

Figure 7:
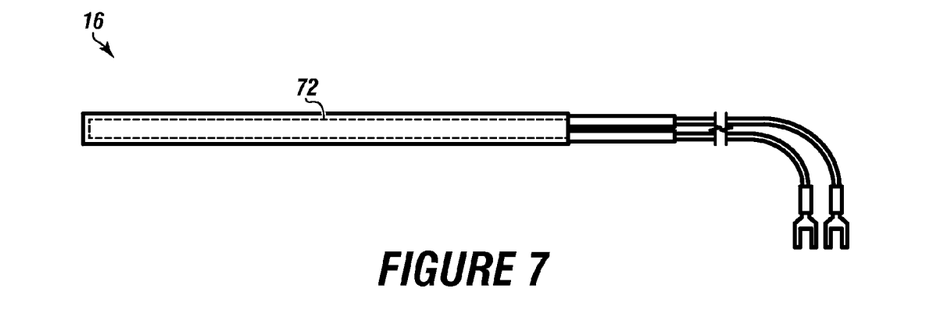
FIG. 7 depicts a perspective view of a heating element.

FIG. 7 depicts a perspective view of the heating element.

In embodiments, the heating element 16 can be a cartridge heater. In embodiments, the heating element can produce from about 70 watts to about 120 watts and can use voltages selected from the group: 24 volts DC current, 120 volts AC current, and 240 volts AC current.

The heating element 16 can include an integrated temperature measurement device 72 for connecting to a network, a display, or both the network and the display. The network can be the internet or any network known in the industry. The display can be a client device display, such as a screen of a computer, a laptop, a smart phone, a cellular telephone, a tablet, or any display known in the industry.

Figure 8:
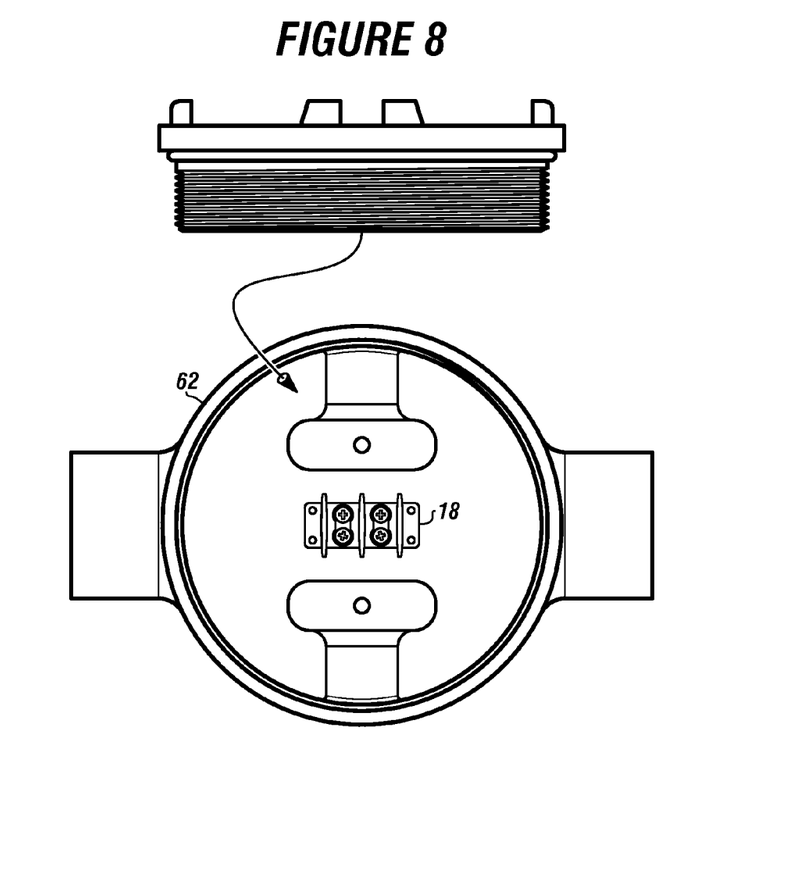
FIG. 8 depicts an assembly view of a junction box.

FIG. 8 depicts an assembly view of the junction box.

The heating element can be adapted to mount in the thermowell bore and connect to a power connection 18 in the junction box 62. When the heating element is energized, the heating element can heat the thermowell.

Figure 9:
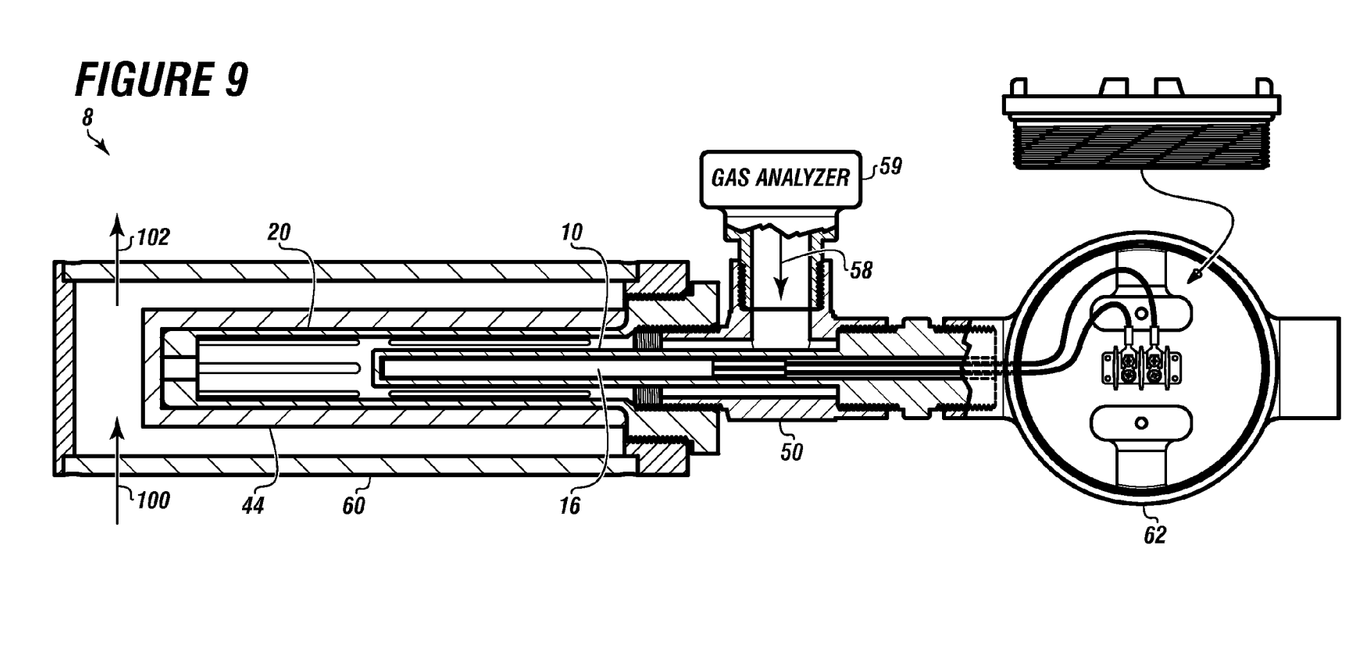
FIG. 9 depicts a cross sectional view of an assembled probe assembly.

FIG. 9 depicts a cross sectional view of an assembled probe assembly.

The probe assembly 8 can engage a gas analyzer 59 producing an outlet gas 58. The outlet gas from the gas analyzer can use a volatile carrier gas. The street tee 50 can connect to the gas analyzer 59.

The sintered metal outer housing 60 can threadably engage the outer threads of the mounting nut while simultaneously enclosing the catalyst cartridge 44, while mounted over the one piece non-sintered metal probe 20.

The outlet gas 58 containing hydrocarbon products with a carrier gas can be received from the gas analyzer 59. The outlet gas 58 can be continuously flowed between the thermowell 10 and the tubular body into the catalyst cartridge 44 for reaction, producing water vapor and carbon dioxide 102. The sintered metal outer housing 60 can simultaneously allow two-way gas flow of ambient air 100 into the catalyst cartridge while exhausting water vapor and carbon dioxide 102 to the atmosphere.

The heating element 16 can be adapted to mount in the thermowell 10. The thermowell 10 can connect to the junction box 62, which can have a removable lid.

In embodiments, the gas analyzer can be a gas chromatograph, a British thermal unit (BTU) analyzer, a spectrophotometer, a mass spectrometer, a tunable diode laser analyzer, an oxygen analyzer, or a similar analyzer known in the industry.

In further embodiments, the volatile carrier gas can be at least one of: a hydrogen, an oxygen, air, a natural gas, ethylene, propylene, and combinations thereof. If two gasses are used at the carrier, the ratio can be 50:50 for each gas however, the carrier depends upon which analyzer is being used.

In embodiments, the probe assembly can have an overall length from about 6 inches to about 14 inches, but not shorter than the length of the thermowell. In further embodiments, the tubular body can have a length from about 4 inches to about 8 inches, and a tubular body inner diameter from about 1/2 of an inch to about 1 inch.

In embodiments, a difference in diameters between the thermowell and the tubular body can be adequated to provide zero backpressure to the gas analyzer and to provide a flow path between the tubular body and the thermowell.

The probe assembly produces no backpressure of outlet gas to the gas analyzer to a constant value creating a continuous flow rate of outlet gas for conversion to carbon dioxide and water vapor at a volume from about 200 milliliters to about 1 liter per minute. In embodiments, the constant value can be atmospheric pressure.

In an embodiment, the probe assembly can have from 2 to 8 hex flats formed on edges of the mounting nut.

To use the probe assembly, the probe assembly can be secured to an outdoor mounting device, such as a rack, a pipe, or structure like a temporary building.

The junction box of the probe assembly can be wired to a power source, such as 110 volts AC from a grid.

A tube from a gas analyzer can be connected to the inlet port of the street tee of the probe assembly. Gas from the gas analyzer vent can then be flowed from the gas analyzer to the probe assembly.

Power can then be turned on, causing the heating element to heat the thermowell to temperatures from about 80 degrees centigrade to about 110 degrees centigrade, which in turn can provide heat to the incoming gas as it swirls between the thermowell and the one piece non-sintered metal probe.

Hydrocarbons in the incoming gas stream from the gas analyzer can be converted to water vapor and carbon dioxide in a catalytic reaction using the catalyst cartridge. The catalytic reaction can be supported by atmospheric air entering through the sintered metal outer housing to the space between the catalytic cartridge and the sintered metal outer housing while water vapor and carbon dioxide are emitted through the sintered metal outer housing created by the catalytic reaction.

The probe assembly can allow gas from the gas analyzer to be processed continuously in volumes of about 200 milliliters to about 1 liter per minute.

Only annual replacement of the catalyst cartridge can be needed to ensure a full conversion of the hydrocarbon products to water vapor and carbon dioxide. Prior to replacing the catalyst cartridge, the probe assembly can be de-energized and allowed to cool. The sintered metal outer housing can then be unscrewed from the one piece non-sintered metal probe and removed. The catalyst cartridge can then be removed from the one piece non-sintered metal probe and replaced with a new catalyst cartridge. The sintered metal outer housing can then be re-threaded onto the one piece non-sintered metal probe for re-energizing and continued long reliable operation.

While these embodiments have been described with emphasis on the embodiments, it should be understood that within the scope of the appended claims, the embodiments might be practiced other than as specifically described herein.

What is claimed is:

1. A probe assembly for processing an outlet gas from a gas analyzer, wherein the outlet gas contains a volatile carrier gas, and wherein the probe assembly comprises:
   a. a thermowell with a thermowell bore;
   b. a heating element adapted to mount in the thermowell bore, the heating element connecting to a power connection and when energized, the heating element heats the thermowell;
   c. a one piece non-sintered metal probe comprising:
      (i) a mounting nut with an inner threaded bore, outer threads and an outer thread outer diameter; and
      (ii) a tubular body with a tubular body outer diameter integral with the mounting nut, wherein the tubular body outer diameter is smaller than the mounting nut and outer thread outer diameter, the tubular body further comprising:
         1. an outer surface;
         2. a tubular body inner bore;
         3. an end cap with an end cap inner bore, wherein the end cap inner bore fluidly connects to the tubular body inner bore, and the end cap has an end cap inner bore diameter that is smaller than a tubular body inner diameter;
         4. a plurality of upper longitudinal outer grooves formed around the end cap with each upper longitudinal outer groove penetrating to the tubular body inner bore without penetrating to the end cap inner bore; and
         5. a plurality of longitudinal slots, each of the plurality of longitudinal slot extending from the outer surface to the tubular body inner bore;
   d. a catalyst cartridge with a central cavity, wherein the tubular body has an interference fit within the central cavity and rests on the mounting nut;
   e. a street tee with a first tee end, a second tee end, and an inlet port, wherein the first tee end threadably engages the thermowell, the second tee end threadably engages the inner threaded bore of the mounting nut, and the inlet port is adapted to receive the outlet gas from the gas analyzer;
   f. a sintered metal outer housing threadably engaging the outer threads of the mounting nut while simultaneously enclosing the catalyst cartridge, wherein the outlet gas containing the volatile carrier gas is received from the gas analyzer and continuously flows between the thermowell and the tubular body into the catalyst cartridge for reaction, the catalyst cartridge producing water vapor and carbon dioxide while the sintered metal outer housing simultaneously allows two-way gas flow of an ambient air to the catalyst cartridge while exhausting the water vapor and carbon dioxide; and
   g. a junction box threaded to the thermowell for supplying power to the heating element; and
      wherein the probe assembly produces (i) zero backpressure of outlet gas to the gas analyzer or (ii) outlet gas at a constant value while (iii) continuously flowing outlet gas into the probe assembly for continuous conversion of the outlet gas to water vapor and carbon dioxide at a rate up to 1 liter per minute.

2. The probe assembly of claim 1, wherein the plurality of upper longitudinal outer grooves and the plurality of longitudinal slots are a plurality of individual slots extending from the end cap to the tubular body inner bore.

3. The probe assembly of claim 1, wherein the one piece non-sintered metal probe comprises a tubular non-ferrous corrosion resistant material.

4. The probe assembly of claim 1, wherein the one piece non-sintered metal probe comprises at least one of: from 4 to 8 upper longitudinal outer grooves of the plurality of upper longitudinal outer grooves and from 4 to 8 longitudinal slots of the plurality of longitudinal slots.

5. The probe assembly of claim 1, wherein the one piece non-sintered metal probe comprises the plurality of upper longitudinal outer grooves aligned with the plurality of longitudinal slots.

6. The probe assembly of claim 1, wherein the heating element is a cartridge heater.

7. The probe assembly of claim 1, comprising an integrated temperature measurement device in the heating element, wherein the integrated temperature measurement device connects to a network, a display, or both the network and the display.

8. The probe assembly of claim 1, wherein the heating element produces from 70 watts to 120 watts and uses voltages selected from the group: 24 volts DC current, 120 volts AC current, and 240 volts AC current.

9. The probe assembly of claim 1, wherein the gas analyzer is at least one of: a gas chromatograph, a British Thermal Unit (BTU) analyzer, a spectrophotometer, a mass spectrometer, a tunable diode laser analyzer, and an oxygen analyzer.

10. The probe assembly of claim 1, wherein the volatile carrier gas is at least one of: a hydrogen, an oxygen, an air, a natural gas, an ethylene, a propylene, and combinations thereof.

11. The probe assembly of claim 1, wherein the thermowell and the one piece non-sintered metal probe are at least one of: a stainless steel, a titanium, an alloy of corrosion resistant material, a ceramic, a ceramic and glass, and combinations thereof.

12. The probe assembly of claim 1, wherein the thermowell bore has an inner diameter from $1/16$ of an inch to $1/4$ of an inch, and the thermowell has a length from 7 inches to 12 inches.

13. The probe assembly of claim 1, wherein a difference in thermowell diameter and tubular body diameter provide zero backpressure to the gas analyzer while simultaneously providing a flow path between the tubular body and the thermowell.

14. The probe assembly of claim 1, wherein the constant value of the outlet gas is atmospheric pressure.

15. The probe assembly of claim 1, wherein the catalyst cartridge is a ceramic wool supported platinum catalyst having a cylindrical shape with an enclosed end cap.

16. The probe assembly of claim 1, wherein the sintered metal outer housing has one of the following: a non-sintered solid end cap, a non-sintered solid threaded end cap, and a sintered metal central portion integral between the non-sintered solid end cap and the non-sintered solid threaded end cap, and wherein the sintered metal central portion comprises 100 percent sintered metal ranging in thickness from ⅛ of an inch to ½ of an inch.

17. The probe assembly of claim 1, wherein the plurality of longitudinal slots have a shape selected from the group: elliptical, round, square, and another polygonal shape.

* * * * *